(12) United States Patent
Jonas et al.

(10) Patent No.: US 6,787,548 B1
(45) Date of Patent: Sep. 7, 2004

(54) THIENOPYRIMIDINES AS PHOSPHODIESTERASE INHIBITORS

(75) Inventors: Rochus Jonas, Darmstadt (DE); Pierre Schelling, Muhltal (DE); Franz-Werner Kluxen, Darmstadt (DE); Maria Christadler, Rodermark (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 109 days.

(21) Appl. No.: 10/018,484

(22) PCT Filed: Jun. 7, 2000

(86) PCT No.: PCT/EP00/05278

§ 371 (c)(1),
(2), (4) Date: May 10, 2002

(87) PCT Pub. No.: WO00/78767

PCT Pub. Date: Dec. 28, 2000

(30) Foreign Application Priority Data

Jun. 19, 1999 (DE) .......................... 199 28 146

(51) Int. Cl.$^7$ .................... A61K 31/505; C07D 495/04
(52) U.S. Cl. ...................... 514/250; 544/267
(58) Field of Search ........................ 544/250; 514/267

(56) References Cited

U.S. PATENT DOCUMENTS 6,495,557 B1  12/2002  Jonas et al. ............... 514/267

FOREIGN PATENT DOCUMENTS

DE   196 44228 A   4/1998
DE   198 19023 A   11/1999

*Primary Examiner*—Richard L. Raymond
(74) *Attorney, Agent, or Firm*—Millen, White, Zelano & Branigan, P.C.

(57) ABSTRACT

Thienopyrimidines of the formula I

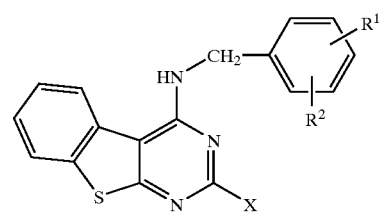

and their physiologically acceptable salts, in which $R^1$, $R^2$ and X have the meanings indicated in claim 1, exhibit phosphodiesterase V inhibition and can be employed for the treatment of disorders of the cardiovascular system and for the treatment and/or therapy of potency disorders.

21 Claims, No Drawings

THIENOPYRIMIDINES AS PHOSPHODIESTERASE INHIBITORS

This application is 371 of PCT/EP00/05278, filed Jun. 7, 2000.

The invention relates to compounds of the formula I

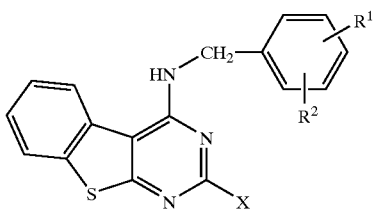

in which
$R^1$, $R^2$ in each case independently of one another are H, A, OH, OA or Hal,
X is $R^4$, $R^5$ or $R^6$, which is monosubstituted by $R^7$,
$R^4$ is linear or branched alkylene having 1–10 C atoms, in which one or two $CH_2$ groups can be replaced by —CH=CH— groups,
$R^5$ is cycloalkyl or cycloalkyl alkylene having 5–12 C atoms,
$R^6$ is phenyl or phenylmethyl,
$R^7$ is COOH, COOA, $CONH_2$, CONHA, $CON(A)_2$ or CN,
A is alkyl having 1 to 6 C atoms and
Hal is F, Cl, B3r or I, where at least one of the radicals $R^1$ or $R^2$ is OH, and their physiologically acceptable salts.

Pyrimidine derivatives have been disclosed, for example, in EP 201 188 or WO 93/06104.

The invention is based on the object of finding novel compounds having valuable properties, in particular those which can be used for the production of medicaments.

It has been found that the compounds of the formula I and their salts have very valuable pharmacological properties together with good tolerability.

In particular, they exhibit a specific inhibition of cGMP phosphodiesterase (PDE V).

Quinazolines having cGMP phosphodiesterase-inhibiting activity are described, for example, in J. Med. Chem. 36, 3765 (1993) and ibid. 37, 2106 (1994).

The biological activity of the compounds of the formula I can be determined by methods such as are described, for example, in WO 93/06104. The affinity of the compounds according to the invention for cGMP and cAMP phosphodiesterase is determined by the ascertainment of their $IC_{50}$ values (concentration of the inhibitor which is needed in order to achieve a 50% inhibition of the enzyme activity). For carrying out the determinations, enzymes isolated according to known methods can be used (e.g. W. J. Thompson et al., Biochem. 1971, 10, 311). For carrying out the experiments, a modified "batch" method of W. J. Thompson and M. M. Appleman (Biochem. 1979, 18, 5228) can be used.

The compounds are therefore suitable for the treatment of disorders of the cardiovascular system, in particular cardiac insufficiency, and for the treatment and/or therapy of potency disorders (erectile dysfunction).

The use of substituted pyrazolopyrimidinones for the treatment of impotence is described, for example, in WO 94/28902.

The compounds are effective as inhibitors of the phenylephrine-induced contractions in corpus cavernosum preparations of hares. This biological action can be demonstrated, for example, according to the method which is described by F. Holmquist et al. in J. Urol., 150, 1310–1315 (1993). The inhibition of the contraction shows the efficacy of the compounds according to the invention for the therapy and/or treatment of potency disorders.

The compounds of the formula I can be employed as pharmaceutical active compounds in human and veterinary medicine. In addition, they can be employed as intermediates for the preparation of further pharmaceutical active compounds.

The invention accordingly relates to the compounds of the formula I and to a process for the preparation of compounds of the formula I according to claim 1 and their salts, characterized in that
a) a compound of the formula II

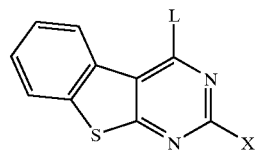

in which
X has the meaning indicated,
and L is Cl, Br, OH, $SCH_3$ or a reactive esterified OH group, is reacted with a compound of the formula III

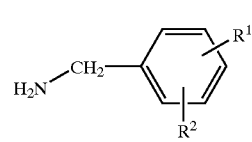

in which
$R^1$ and $R^2$ have the meanings indicated, or
b) in a compound of the formula I, a radical X is converted into another radical X by hydrolysing an ester group to a COOH group or converting a COOH group into an amide or into a cyano group
or
c) in a compound of the formula I, a radical $R^1$ and/or $R^2$ is converted into another radical $R^1$ and/or $R^2$ by converting an alkoxy group into a hydroxyl group, and/or a compound of the formula I is converted into one of its salts.

Above and below, the radicals $R^1$, $R^2$, $R^3$, $R^4$, $R^5$, $R^6$, $R^7$, X and L have the meanings indicated in the formulae I, II and III, if not expressly stated otherwise.

A is alkyl having 1–6 C atoms. In the above formulae, alkyl is preferably unbranched and has 1, 2, 3, 4, 5 or 6 C atoms and is preferably methyl, ethyl or propyl, furthermore preferably isopropyl, butyl, isobutyl, sec-butyl or tert-butyl, but also n-pentyl, neopentyl, isopentyl or hexyl.

X is an $R^4$, $R^5$ or $R^6$ radical which is monosubstituted by $R^7$.

$R^4$ is a linear or branched alkylene radical having 1–10 C atoms, where the alkylene radical is preferably, for example, methylene, ethylene, propylene, isopropylene, butylene, isobutylene, sec-butylene, pentylene, 1-, 2- or 3-methylbutylene, 1,1-, 1,2- or 2,2-dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, linear or branched heptylene, octylene, nonylene or decylene. $R^4$ is furthermore, for example, but-2-enylene or hex-3-enylene. Ethylene, propylene or butylene is very particularly preferred.

$R^5$ is cycloalkylalkylene having 5–12 C atoms, preferably, for example, cyclopentylmethylene, cyclohexylmethylene, cyclohexylethylene, cyclohexyl-propylene or cyclohexylbutylene. $R^5$ is also cycloalkyl preferably having 5–7 C atoms. Cycloalkyl is, for example, cyclopentyl, cyclohexyl or cycloheptyl.

Hal is preferably F, Cl or Br, but also I.

The radicals $R^1$ and $R^2$ can be identical or different and are preferably in the 3- or 4-position of the phenyl ring. They are, for example, in each case independently of one another H, alkyl, alkoxy, hydroxyl, F, Cl, Br or I. Preferably, they are independently of one another Hal and hydroxyl. At least one of the radicals $R^1$ and $R^2$ is hydroxyl.

The radical $R^7$ is preferably, for example, COOH, $COOCH_3$, $COOC_2H_5$, $CONH_2$, $CON(CH_3)_2$, $CONHCH_3$ or CN.

It applies to the whole invention that all radicals which occur a number of times can be identical or different, i.e. are independent of one another.

Accordingly, the invention relates in particular to those compounds of the formula I in which at least one of the radicals mentioned has one of the preferred meanings indicated above.

Some preferred groups of compounds can be expressed by the following subformulae Ia to Id, which correspond to the formula I and in which the radicals not designated in greater detail have the meaning indicated in the formula I, but in which in Ia
  X is $R^4$, phenyl or phenylmethyl, which is substituted by COOH, COOA, $CONH_2$, $CONA_2$, CONHA or CN;
in Ib
  $R^1$, $R^2$ in each case independently of one another are H, A, OH, OA or Hal,
  X is $R^4$, phenyl or phenylmethyl, which is substituted by COOH, COOA, $CONH_2$, $CONA_2$, CONHA or CN;
  where at least one of the radicals $R^1$ and $R^2$ is OH;
in Ic
  $R^1$, $R^2$ in each case independently of one another are H, A, OA or Hal,
  X is alkylene having 2–5 C atoms, cyclohexyl, phenyl or phenylmethyl, which is monosubstituted by $R^7$,
  $R^7$ is COOH or COOA,
  A is alkyl having 1–6 C atoms,
  Hal is F, Cl, Br or I,
  where at least one of the radicals $R^1$ and $R^2$ is OH;
in Id
  $R^1$ is Hal,
  $R^2$ is OH,
  X is alkylene having 2–5 C atoms, cyclohexyl, phenyl or phenylmethyl, which is monosubstituted by $R^7$,
  $R^7$ is COOH or COOA,
  A is alkyl having 1–6 C atoms,
  Hal is F, Cl, Br or I,
and their physiologically acceptable salts.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. Use can also be made in this case of variants which are known per se, but not mentioned here in greater detail.

In the compounds of the formula II or III, $R^1$, $R^2$, $R^3$, $R^4$, X and n have the meanings indicated, in particular the preferred meanings indicated.

If L is a reactive esterified OH group, this is preferably alkylsulfonyloxy having 1–6 C atoms (preferably methylsulfonyloxy) or arylsulfonyloxy having 6–10 C atoms (preferably phenyl- or p-tolylsulfonyloxy, in addition also 2-naphthalenesulfonyloxy).

The compounds of the formula I can preferably be obtained by reacting compounds of the formula II with compounds of the formula III.

If desired, the starting substances can also be formed in situ, such that they are not isolated from the reaction mixture, but immediately reacted further to give the compounds of the formula I. On the other hand, it is possible to carry out the reaction stepwise.

As a rule, the starting compounds. of the formulae II and III are known. If they are not known, they can be prepared by methods known per se. Compounds of the formula II can be obtained, e.g. by reaction with $POCl_3$, from the corresponding hydroxypyrimidines, which are synthesized from thiophene derivatives and CN-substituted alkylene carboxylic acid esters. (Eur. J. Med. Chem. 23,. 453 (1988)). The hydroxypyrimidines are prepared either by dehydrogenation of corresponding tetrahydrobenzo-thienopyrimidine compounds or by the cyclization of 2-aminobenzothiophene-3-carboxylic acid derivatives with aldehydes or nitrites, which is customary for the prepartion of pyrimidine derivatives (e.g. Houben Weyl E9b/2).

Specifically, the reaction of the compounds of the formula II with the compounds of the formula III is carried out in the presence or the absence of an inert solvent at temperatures between approximately −20 and approximately 150°, preferably between 20 and 100°.

The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylamine, pyridine or quinoline, or an excess of the amine components can be favourable.

Suitable inert solvents are, for example, hydrocarbons such as hexane, petroleum ether, benzene, toluene or xylene; chlorinated hydrocarbons such as trichloroethylene, 1,2-dichloroethane, carbontetra-chloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide, N-methylpyrrolidone or dimethyl-formamide (DMF); nitriles such as acetonitrile; sulfoxides such as dimethyl sulfoxide (DMSO); nitro compounds such as nitromethane or nitrobenzene; esters such as ethyl acetate or mixtures of the solvents mentioned.

It is furthermore possible to convert a radical X in a compound of the formula I into another radical X, e.g. by hydrolysing an ester or a cyano group to a COOH group.

Ester groups can be hydrolysed, for example, using NaOH or KOH in water, water-THF or water-dioxane at temperatures between 0 and 100°.

Carboxylic acids can be converted, for example using thionyl chloride, into the corresponding carboxylic acid chlorides and these can be converted into carboxamides. By elimination of water in a known manner, carbonitriles are obtained from these. Compounds of the formula I in which $R^1$ and/or $R^2$ are OA can be converted according to known methods of ether cleavage into the corresponding compounds of the formula I in which $R^1$ and/or $R^2$ is hydroxyl.

An acid of the formula I can be converted into the associated acid addition salt using a base, for example by reaction of equivalent amounts of the acid and of the base in an inert solvent such as ethanol and subsequent evaporation. Suitable bases for this reaction are in particular those which yield physiologically acceptable salts. Thus the acid of the formula I can be converted into the corresponding metal salt, in particular alkali metal or alkaline earth metal salt, or into the corresponding ammonium salt using a base (e.g. sodium or potassium hydroxide or carbonate). For this reaction, suitable organic bases are in particular also those which yield physiologically acceptable salts, such as, for example, ethanolamine.

On the other hand, a base of the formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid. Salts with physiologically unacceptable acids, e.g. picrates, can be used for the isolation and/or purification of the compounds of the formula I.

The invention furthermore relates to the use of the compounds of the formula I and/or their physiologically acceptable salts for the production of pharmaceutical preparations, in particular by a non-chemical route. In this connection, they can be brought into a suitable dose form together with at least one solid, liquid and/or semi-liquid vehicle or excipient and, if appropriate, in combination with one or more further active compounds.

The invention also relates to medicaments of the formula I and their physiologically acceptable salts as phosphodiesterase V inhibitors.

The invention further relates to pharmaceutical preparations, comprising at least one compound of the formula I and/or one of its physiologically acceptable salts.

These preparations can be used as medicaments in human or veterinary medicine. Suitable vehicles are organic or inorganic substances which are suitable for enteral (e.g. oral) or parenteral administration or topical application and do not react with the novel compounds, for example water, vegetable oils, benzyl alcohols, alkylene glycols, polyethylene glycols, glyceryl triacetate, gelatine, carbohydrates such as lactose or starch, magnesium stearate, talc and petroleum jelly. In particular, tablets, pills, coated tablets, capsules, powders, granules, syrups, juices or drops are used for oral administration, suppositories are used for rectal administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain excipients such as lubricants, preservatives, stabilizers and/or wetting agents, emulsifiers, salts for influencing the osmotic pressure, buffer substances, colourants, flavourings and/or one or more further active compounds, e.g. one or more vitamins.

The compounds of the formula I and their physiologically acceptable salts can be employed in the control of diseases in which an increase in the CGMP (cyclic guanosin monophosphate) level leads to inhibition or prevention of inflammation and muscle relaxation. The compounds according to the invention can particularly be used in the treatment of diseases of the cardiovascular system and for the treatment and/or therapy of potency disorders.

In this connection, the substances are as a rule preferably administered in doses of between approximately 1 and 500 mg, in particular between 5 and 100 mg, per dose unit. The daily dose is preferably between approximately 0.02 and 10 mg/kg of body weight. The specific dose for each patient depends, however, on all sorts of factors, for example on the efficacy of the specific compound employed, on the age, body weight, general state of health, sex, on the diet, on the time and route of administration, and on the excretion rate, pharmaceutical combination and severity of the particular disorder to which the therapy applies. Oral administration is preferred.

Above and below, all temperatures are indicated in ° C. In the following examples, "customary working-up" means: if necessary, water is added, the pH is adjusted, if necessary, depending on the constitution of the final product, to a value of between 2 and 10, the mixture is extracted with ethyl acetate or dichloromethane, the organic phase is separated off, dried over sodium sulfate and evaporated, and the residue is purified by chromatography on silica gel and/or by crystallization.

Mass spectrometry (MS): EI (electron impact ionization) $M^+$

FAB (fast atom bombardment) $(M+H)^+$

EXAMPLE 1

Methyl 3-(4-chlorobenzothieno[2,3-d]pyrimidin-2-yl) propionate [obtainable by cyclization of methyl 2-amino-5, 6,7,8-tetrahydrobenzothiophene-3-carboxylate with methyl 3-cyanopropionate, dehydrogenation with sulfur and subsequent chlorination with phosphorus oxychloride/ dimethylamine] and 3-chloro-4-methoxybenzylamine ("A") in N-methylpyrrolidone are stirred at 110° for 5 hours. The solvent is removed and the residue is worked up in the customary manner. Methyl 3-[4-(3-chloro-4-methoxybenzylamino)benzothieno-[2,3-d]pyrimidin-2-yl] propionate is obtained as a colourless oil.

The following is obtained analogously by reaction of "A"

with methyl 2-(4-chlorobenzothieno[2,3-d]pyrimidin-2-yl) acetate
methyl 2-[4-(3-chloro-4-methoxybenzylamino)benzothieno[2,3-d]pyrimidin-2-yl]acetate.

The following is obtained analogously by reaction of "A"

with methyl 4-(4-chlorobenzothieno[2,3-d]pyrimidin-2-yl) butyrate
methyl 4-[4-(3-chloro-4-methoxybenzylamino)benzo-thieno[2,3-d]pyrimidin-2-yl]butyrate.

The following is obtained analogously by reaction of "A"

with methyl 5-(4-chlorobenzothieno[2,3-d]pyrimidin-2-yl) valerate
methyl 5-[4-(3-chloro-4-methoxybenzylamino)benzo-thieno[2,3-d]pyrimidin-2-yl]valerate.

The following is obtained analogously by reaction of "A"

with methyl 7-(4-chlorobenzothieno[2,3-d]pyrimidin-2-yl) heptanoate
methyl 7-[4-(3-chloro-4-methoxybenzylamino)benzo-thieno[2,3-d]pyrimidin-2-yl]heptanoate.

The following is obtained analogously by reaction of "A"

with methyl 2-[4-(4-chlorobenzothieno[2,3-d]pyrimidin-2-yl)cyclohex-1-yl]acetate
methyl 2-(4-[4-(3-chloro-4-methoxybenzylamino)-benzothieno[2,3-d]pyrimidin-2-yl]cyclohex-1-yl)acetate The following is obtained analogously by reaction of "A"

with methyl 4-(4-chlorobenzothieno[2,3-d]pyrimidin-2-yl) cyclohexanecarboxylate
methyl 4-[4-(3-chloro-4-methoxybenzylamino)benzo-thieno[2,3-d]pyrimidin-2-yl]cyclohexanecarboxylate.

EXAMPLE 2

Methyl 3-[4-(3-chloro-4-methoxybenzylamino) benzothieno-[2,3-d]pyrimidin-2-yl]propionate is dissolved in ethylene glycol monomethyl ether and stirred at 110° for 5 hours after addition of 32% NaOH. After addition of 20% HCl, the mixture is extracted with dichloromethane. By addition of petroleum ether, 3-[4-(3-chloro-4-methoxybenzylamino)benzothieno[2,3-d]-pyrimidin-2-yl]propionic acid, m.p. 218°, is obtained.

The precipitated crystals are dissolved in isopropanol and treated with ethanolamine. After crystallization, 3-[4-(3-chloro-4-methoxybenzylamino)-benzothieno[2,3-d]pyrimidin-2-yl]propionic acid, ethanolamine salt, is obtained.

The compounds

4-[4-(3-chloro-4-methoxybenzylamino)benzothieno-[2,3-d]pyrimidin-2-yl]butyric acid, m.p. 225°; ethanolamine salt m.p. 150°;
5-[4-(3-chloro-4-methoxybenzylamino)benzothieno-[2,3-d]pyrimidin-2-yl]valeric acid, m.p. 210°, ethanolamine salt m.p. 141° are obtained analogously.
The carboxylic acids below are obtained analogously from the esters listed under Example 1:

2-[4-(3-chloro-4-methoxybenzylamino)benzothieno-[2,3-d]pyrimidin-2-yl]acetic acid,
7-[4-(3-chloro-4-methoxybenzylamino)benzothieno-[2,3-d]pyrimidin-2-yl]heptanoic acid, 2-{4-[4-(3-chloro-4-methoxybenzylamino)benzo-thieno[2,3-d]pyrimidin-2-yl]cyclohex-1-yl}acetic acid, 4-[4-(3-chloro-4-methoxybenzylamino)benzothieno-[2,3-d]pyrimidin-2-yl]cyclohexanecarboxylic acid, ethanolamine salt, m.p. 167°.

EXAMPLE 3

A mixture of 1.5 g of methyl 4-(4-chlorobenzothieno[2,3-d]pyrimidin-2-yl)phenylcarboxylate ("B"), prepared by dehydrogenation of the corresponding 5,6,7,8-tetrahydrobenzothieno[2,3-d]pyrimidine compound with sulfur and subsequent chlorination with phosphorus oxychloride/dimethylamine, and 1.5 g of 3-chloro-4-methoxybenzylamine in 20 ml of N-methylpyrrolidone is heated at 110° for 4 hours. After cooling, the mixture is worked up in the customary manner. 2.6 g of methyl 4-[4-(3-chloro-4-methoxybenzylamino)benzothieno[2,3-d]pyrimidin-2-yl]-benzoate, m.p. 203–204°, are obtained.

Analogously to Example 2, 1.0 g of 4-[4-(3-chloro-4-methoxybenzylamino)benzothieno-[2,3-d]pyrimidin-2-yl]benzoic acid, ethanolamine salt, m.p. 189–190°, are obtained from 1.2 g of the ester thereof.

The compound 4-[4-(3-chloro-4-methoxybenzyl-amino)benzothieno[2,3-d]pyrimidin-2-yl]phenylacetic acid, ethanolamine salt, m.p. 130°, is obtained analogously.

EXAMPLE 4

1 equivalent of 3-[4-(3-chloro-4-methoxybenzyl-amino) benzothieno[2,3-d]pyrimidin-2-yl]propionic acid and 1.2 equivalents of thionyl chloride are stirred in dichloromethane for 2 hours. The solvent is removed and 3-[4-(3-chloro-4-methoxybenzylamino)benzothieno[2,3-d]-pyrimidin-2-yl]propionyl chloride is obtained. The mixture is transferred to aqueous ammonia, stirred for one hour and, after customary working up, 3-[4-(3-chloro-4-methoxybenzylamino)benzothieno[2,3-d]pyrimidin-2-yl] propionamide is obtained.

EXAMPLE 5

1 equivalent of DMF and 1 equivalent of oxalyl chloride are dissolved in acetonitrile at 0°. 1 equivalent of 3-[4-(3-chloro-4-methoxybenzylamino)-benzothieno[2,3-d]pyrimidin-2-yl]propionamide is then added. The mixture is subsequently stirred for one hour. After customary working up, 3-[4-(3-chloro-4-methoxybenzylamino)benzothieno[2,3-d]pyrimidin-2-yl]-propionitrile is obtained.

EXAMPLE 6

The compounds obtained in Examples 1 to 5 can be converted into the corresponding hydroxyl compounds by known methods of ether cleavage. The compounds below methyl 3-[4-(3-chloro-4-hydroxybenzylamino)benzo-thieno [2,3-d]pyrimidin-2-yl]propionate,
methyl 2-[4-(3-chloro-4-hydroxybenzylamino)benzo-thieno [2,3-d]pyrimidin-2-yl]acetate,
methyl 4-[4-(3-chloro-4-hydroxybenzylamino)benzo-thieno [2,3-d]pyrimidin-2-yl]butyrate,
methyl 5-[4-(3-chloro-4-hydroxybenzylamino)benzo-thieno [2,3-d]pyrimidin-2-yl]valerate,
methyl 7-[4-(3-chloro-4-hydroxybenzylamino)benzo-thieno [2,3-d]pyrimidin-2-yl]heptanoate,
methyl 2-(4-[4-(3-chloro-4-hydroxybenzylamino)-benzothieno[2,3-d]pyrimidin-2-yl]cyclohex-1-yl]acetate, methyl 4-[4-(3-chloro-4-hydroxybenzylamino)benzo-thieno[2,3-d]pyrimidin-2-yl]cyclohexanecarboxylate,
3-[4-(3-chloro-4-hydroxybenzylamino)benzothieno-[2,3-d]pyrimidin-2-yl]propionic acid,
4-[4-(3-chloro-4-hydroxybenzylamino)benzothieno-[2,3-d]pyrimidin-2-yl]butyric acid,
5-[4-(3-chloro-4-hydroxybenzylamino)benzothieno-[2,3-d]pyrimidin-2-yl]valeric acid,
2-[4-(3-chloro-4-hydroxybenzylamino)benzothieno-[2,3-d]pyrimidin-2-yl]acetic acid,
7-[4-(3-chloro-4-hydroxybenzylamino)benzothieno-[2,3-d]pyrimidin-2-yl]heptanoic acid,
2-(4-[4-(3-chloro-4-hydroxybenzylamino)benzo-thieno[2,3-d]pyrimidin-2-yl]cyclohex-1-yl)acetic acid,
4-[4-(3-chloro-4-hydroxybenzylamino)benzothieno-[2,3-d]pyrimidin-2-yl]cyclohexanecarboxylic acid,
4-[4-(3-chloro-4-hydroxybenzylamino)benzothieno-[2,3-d]pyrimidin-2-yl]benzoic acid,
4-[4-(3-chloro-4-hydroxybenzylamino)benzothieno-[2,3-d]pyrimidin-2-yl]phenylacetic acid,
3-[4-(3-chloro-4-hydroxybenzylamino)benzothieno-[2,3-d]pyrimidin-2-yl]propionamide,
3-[4-(3-chloro-4-hydroxybenzylamino)benzothieno-[2,3-d]pyrimidin-2-yl]propionitrile, are thus obtained.

EXAMPLE 7

Analogously to Example 1, by reaction of 0.01 mol of methyl 4-(4-chlorobenzothieno[2,3-d]pyrimidin-2-yl)cyclohexanecarboxylate with 0.02 mol of 3-chloro-4-hydroxybenzylamine in 40 ml of 1-methyl-2-pyrrolidone, after customary working up methyl 4-[4-(3-chloro-4-hydroxybenzylamino)benzo-thieno[2,3-d]pyrimidin-2-yl]cyclohexanecarboxylate is obtained.

The compounds methyl 4-[4-(3-methoxy-4-hydroxybenzylamino)benzothieno[2,3-d]pyrimidin-2-yl]cyclohexanecarboxylate and
methyl 4-[4-(4-hydroxybenzylamino)benzothieno-[2,3-d]pyrimidin-2-yl]cyclohexanecarboxylate are obtained analogously.

By ester hydrolysis analogously to Example 2, the compounds

4-[4-(3-chloro-4-hydroxybenzylamino)benzothieno-[2,3-d]pyrimidin-2-yl]cyclohexanecarboxylic acid, ethanolamine salt, m.p. 200–202°;
4-[4-(3-methoxy-4-hydroxybenzylamino)benzothieno-[2,3-d]pyrimidin-2-yl]cyclohexanecarboxylic acid,
4-[4-(4-hydroxybenzylamino)benzothieno[2,3-d]pyrimidin-2-yl]cyclohexanecarboxylic acid are obtained therefrom.

The compounds below

4-[4-(3-methoxy-4-hydroxybenzylamino)benzothieno-[2,3-d]pyrimidin-2-yl]butyric acid,
5-[4-(3-methoxy-4-hydroxybenzylamino)benzothieno-[2,3-d]pyrimidin-2-yl]valeric acid,
2-[4-(3-methoxy-4-hydroxybenzylamino)benzothieno-[2,3-d]pyrimidin-2-yl]acetic acid,
7-[4-(3-methoxy-4-hydroxybenzylamino)benzothieno-[2,3-d]pyrimidin-2-yl]heptanoic acid,
2-{4-[4-(3-methoxy-4-hydroxybenzylamino)benzo-thieno[2,3-d]pyrimidin-2-yl]cyclohex-1-yl}acetic acid,
4-[4-(4-hydroxybenzylamino)benzothieno[2,3-d]-pyrimidin-2-yl]butyric acid,
5-[4-(4-hydroxybenzylamino)benzothieno[2,3-d]-pyrimidin-2-yl]valeric acid,
2-[4-(4-hydroxybenzylamino)benzothieno[2,3-d]-pyrimidin-2-yl]acetic acid,
7-[4-(4-hydroxybenzylamino)benzothieno[2,3-d]-pyrimidin-2-yl]heptanoic acid,
2-{4-[4-(4-hydroxybenzylamino)benzothieno[2,3-d]-pyrimidin-2-yl]cyclohex-1-yl}acetic acid,
3-{4-[4-(4-hydroxybenzylamino)benzothieno[2,3-d]-pyrimidin-2-yl]cyclohex-1-yl}propionic acid are obtained analogously.

The following examples relate to pharmaceutical preparations:

Example A

Injection vials

A solution of 100 g of an active compound of the formula I and 5 g of disodium hydrogenphosphate is adjusted to pH 6.5 in 3 l of double-distilled water using 2 N hydrochloric acid, sterile filtered, dispensed into injection vials, lyophilized under sterile conditions and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water. The solution is adjusted to pH 6.8, made up to 1 l and sterilized by irradiation. This solution can be used in the form of eye drops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F

Coated Tablets

Analogously to Example E, tablets are pressed and are then coated in a customary manner with a coating of sucrose, potato starch, talc, tragacanth and colourant.

Example G

Capsules 2 kg of active compound of the formula I are filled into hard gelatine capsules in a customary manner such that each capsule contains 20 mg of the active compound.

Example H
Ampoules

A solution of 1 kg of active compound of the formula I in 60 l of double-distilled water is sterile filtered, dispensed into ampoules, lyophilized under sterile conditions and aseptically sealed. Each ampoule contains 10 mg of active compound.

Example I
Inhalation Spray 14 g of active compound of the formula I is dissoved in 10 l of isotonic NaCl solution and the solution is filled into commercially available spray containers having a pump mechanism. The solution can be sprayed into the mouth or nose. One burst of spray (approximately 0.1 ml) corresponds to a dose of approximately 0.14 mg.

What is claimed is:

1. A compound of formula I or a physiologically acceptable salt thereof

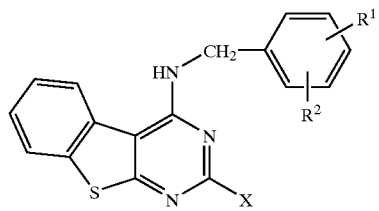

in which
R$^1$, R$^2$ in each case independently of one another are H, A, OH, OA or Hal,
X is R$^4$, R$^5$ or R$^6$, which is monosubstituted by R$^7$,
R$^4$ is linear or branched alkylene having 1–10 C atoms, in which one or two CH$_2$ groups are optionally replaced by —CH=CH— groups,
R$^5$ is cycloalkyl or cycloalkyl alkylene having 5–12 C atoms,
R$^6$ is phenyl or phenylmethyl,
R$^7$ is COOH, COOA, CONH$_2$, CONHA, CON(A)$_2$ or CN,
A is alkyl having 1 to 6 C atoms and
Hal is F, Cl, Br or I,
where at least one of the radicals R$^1$ or R$^2$ is OH.

2. A compound of formula I according to claim 1, that is (a) 3-[4-(3-chloro-4-hydroxybenzylamino)benzo[4,5]thieno[2,3-d]pyrimidin-2-yl]propionic acid;
(b) 7-[4-(3-chloro-4-hydroxybenzylamino)benzo[4,5]thieno[2,3-d]pyrimidin-2-yl]heptanoic acid;
(c) 5-[4-(3-chloro-4-hydroxybenzylamino)benzo[4,5]thieno[2,3-d]pyrimidin-2-yl]valeric acid;
(d) 2-{4-[4-(3-chloro-4-hydroxybenzylamino)benzo[4,5]thieno[2,3-d]pyrimidin-2-yl]cyclohex-1-yl}acetic acid; or
(e) 4-[4-(3-chloro-4-hydroxybenzylamino)benzothieno[2,3-d]pyrimidin-2-yl]cyclohexanecarboxylic acid; or a physiologically acceptable salt thereof.

3. A compound of formula I according to claim 1 or a physiologically acceptable salt thereof, wherein X is R$^4$ or R$^6$.

4. A compound of formula I according to claim 1 or a physiologically acceptable salt thereof, wherein X is alkylene having 2–5 C atoms, cyclohexyl, phenyl or phenylmethyl, and R$^7$ is COOH or COOA.

5. A compound of formula I according to claim 4 or a physiologically acceptable salt thereof, wherein R$^1$ is Hal, and R$^2$ is OH.

6. A process for preparing a compound of formula I according to claim 1 or a salt thereof comprising a) reacting a compound of formula II

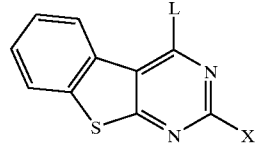

in which
X has the meaning indicated in claim 1,
and L is Cl, Br, OH, SCH$_3$ or a reactive esterified OH group, with a compound of formula III

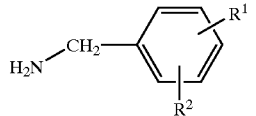

in which
R$^1$ and R$^2$ have the meanings indicated in claim 1, or
b) in a compound of the formula I, a radical X that is an ester group is hydrolyzed to a COOH group or a radical X that is a COOH group is reacted to form into an amide or into a cyano group or
c) in a compound of the formula I, a radical R$^1$ and/or R$^2$ which are alkoxy groups are reacted to form into a hydroxyl group, or a compound of formula I is reacted with an acid or a base to form a salt of a compound of formula I.

7. A process for preparing a pharmaceutical composition comprising bringing together a compound of formula I according to claim 1 or a physiologically acceptable salt thereof with a solid, liquid or semi-liquid vehicle or excipient.

8. A pharmaceutical composition comprising a compound of formula I according to claim 1 or a physiologically acceptable salt thereof and a solid, liquid or semi-liquid vehicle or excipient.

9. A method for controlling a disease of the cardiovascular system comprising administering a pharmaceutical composition according to claim 8 to a patient in need thereof.

10. A method of inhibiting phosphodiesterase V comprising administering a compound of formula I according to claim 1 or a physiologically acceptable salt thereof to a patient in need thereof.

11. A method of inhibiting phosphodiesterase V in vitro comprising bringing together a compound of formula I according to claim 1 or a physiologically acceptable salt thereof with phosphodiesterase V.

12. A method for the treatment or therapy of cardiac insufficiency comprising administering a pharmaceutical composition according to claim 8 to a patient in need thereof.

13. A method for the treatment or therapy of erectile dysfunction comprising administering a pharmaceutical composition according to claim 8 to a patient in need thereof.

14. A pharmaceutical composition comprising a compound of claim 2 or a physiologically acceptable salt thereof and a solid, liquid or semi-liquid vehicle or excipient.

15. A method for controlling a disease of the cardiovascular system comprising administering a pharmaceutical composition according to claim 14 to a patient in need thereof.

16. A method of inhibiting phosphodiesterase V comprising administering a compound of formula I according to claim 2 or a physiologically acceptable salt thereof to a patient in need thereof.

17. A method of inhibiting phosphodiesterase V in vitro comprising bringing together a compound of formula I according to claim 2 or a physiologically acceptable salt thereof with phosphodiesterase V.

18. A method for the treatment or therapy of cardiac insufficiency comprising administering a pharmaceutical composition according to claim 14 to a patient in need thereof.

19. A method for the treatment or therapy of erectile dysfunction comprising administering a pharmaceutical composition according to claim 14 to a patient in need thereof.

20. A method for the treatment or therapy of a potency disorder comprising administering a pharmaceutical composition according to claim 8 to a patient in need thereof.

21. A method for the treatment or therapy of a potency disorder comprising administering a pharmaceutical composition according to claim 14 to a patient in need thereof.

* * * * *